US007559452B2

(12) United States Patent
Wales et al.

(10) Patent No.: US 7,559,452 B2
(45) Date of Patent: Jul. 14, 2009

(54) SURGICAL INSTRUMENT HAVING FLUID ACTUATED OPPOSING JAWS

(75) Inventors: Kenneth S. Wales, Mason, OH (US); Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 35 days.

(21) Appl. No.: 11/165,094

(22) Filed: Jun. 23, 2005

(65) Prior Publication Data

US 2006/0289600 A1 Dec. 28, 2006

Related U.S. Application Data

(63) Continuation-in-part of application No. 11/061,908, filed on Feb. 18, 2005, now abandoned.

(51) Int. Cl.
*A61B 17/072* (2006.01)
*A61B 17/068* (2006.01)

(52) U.S. Cl. .............. 227/176.1; 227/175.1; 227/180.1; 227/19

(58) Field of Classification Search .............. 227/178.1, 227/180.1, 182.1, 19, 176.1; 606/219
See application file for complete search history.

(56) References Cited

U.S. PATENT DOCUMENTS

| | | | | |
|---|---|---|---|---|
| 3,506,005 A | | 4/1970 | Gilio et al. | |
| 4,331,277 A | * | 5/1982 | Green | 227/19 |
| 4,485,817 A | | 12/1984 | Swiggett | |
| 4,488,523 A | | 12/1984 | Shichman | |
| 4,794,912 A | * | 1/1989 | Lia | |
| 4,921,482 A | | 5/1990 | Hammerslag et al. | |
| 5,005,754 A | | 4/1991 | Van Overloop | |
| 5,018,657 A | * | 5/1991 | Pedlick et al. | 227/178.1 |
| 5,179,934 A | | 1/1993 | Nagayoshi et al. | |
| 5,197,649 A | | 3/1993 | Bessler et al. | |
| 5,219,111 A | * | 6/1993 | Bilotti et al. | 227/175.1 |
| 5,250,074 A | * | 10/1993 | Wilk et al. | 606/207 |

(Continued)

FOREIGN PATENT DOCUMENTS

| | | |
|---|---|---|
| EP | 0324635 | 7/1989 |

(Continued)

OTHER PUBLICATIONS

EPO Search Report, Application No. 06253759.2, Nov. 24, 2006, pp. 1-5.

(Continued)

*Primary Examiner*—Rinaldi I. Rada
*Assistant Examiner*—Lindsay Low
(74) *Attorney, Agent, or Firm*—Frost Brown Todd LLC

(57) ABSTRACT

A surgical stapling and severing instrument enables minimally invasive surgical procedures by having upper and lower jaws (i.e., anvil and staple channel) that are positioned with an elongate shaft and handle through surgical openings, and in particular through a cannula of a trocar. A pair of fluid actuator bladders (lift bags) are positioned in the staple channel beneath a proximally projecting lever tray so that transfer of fluid from the handle causes closing and clamping of the anvil. The bi-directional fluid control may be mechanically produced at the handle or by activating an electroactive polymer actuator. Once firing is sensed, an EAP plunger in a medical substance syringe inserted into the elongate shaft is activated to dispense a medical substance (e.g., anesthetics, adhesives, cauterizing substances, antibiotics, etc.) and is guided along a firing bar to a cutting surface of an E-beam placing the substance on tissue as severed.

17 Claims, 12 Drawing Sheets

U.S. PATENT DOCUMENTS

| | | | | |
|---|---|---|---|---|
| 5,275,608 | A | 1/1994 | Forman et al. | |
| 5,314,466 | A | 5/1994 | Stern et al. | |
| 5,339,723 | A * | 8/1994 | Huitema | 91/388 |
| 5,361,583 | A * | 11/1994 | Huitema | 60/413 |
| 5,405,344 | A | 4/1995 | Williamson et al. | |
| 5,411,508 | A | 5/1995 | Bessler et al. | |
| 5,411,519 | A | 5/1995 | Tovey et al. | |
| 5,456,401 | A | 10/1995 | Green et al. | |
| 5,465,895 | A | 11/1995 | Knodel et al. | |
| 5,485,952 | A | 1/1996 | Fontayne | |
| 5,518,164 | A * | 5/1996 | Hooven | 227/5 |
| 5,520,678 | A | 5/1996 | Heckele et al. | |
| 5,547,117 | A | 8/1996 | Hamblin et al. | |
| 5,562,682 | A | 10/1996 | Oberlin et al. | |
| 5,575,799 | A | 11/1996 | Bolanos et al. | |
| 5,620,649 | A | 4/1997 | Trotta | |
| 5,632,433 | A | 5/1997 | Grant et al. | |
| 5,662,662 | A | 9/1997 | Bishop et al. | |
| 5,669,544 | A | 9/1997 | Schulze et al. | |
| 5,673,840 | A | 10/1997 | Schulze et al. | |
| 5,673,841 | A | 10/1997 | Schulze et al. | |
| 5,690,269 | A | 11/1997 | Bolanos et al. | |
| 5,692,668 | A | 12/1997 | Schulze et al. | |
| 5,702,408 | A | 12/1997 | Wales et al. | |
| 5,743,456 | A | 4/1998 | Jones et al. | |
| 5,752,973 | A | 5/1998 | Kieturakis | |
| 5,779,727 | A | 7/1998 | Orejola et al. | |
| 5,797,537 | A | 8/1998 | Oberlin et al. | |
| 5,826,776 | A | 10/1998 | Schulze et al. | |
| 5,829,662 | A | 11/1998 | Allen et al. | |
| 5,865,361 | A | 2/1999 | Milliman et al. | |
| 5,865,831 | A | 2/1999 | Cozean et al. | |
| 5,901,895 | A | 5/1999 | Heaton et al. | |
| 5,918,791 | A * | 7/1999 | Sorrentino et al. | 227/175.3 |
| 6,010,054 | A | 1/2000 | Johnson et al. | |
| 6,460,749 | B1 * | 10/2002 | Levinson et al. | 227/180.1 |
| 6,485,409 | B1 | 11/2002 | Voloshin et al. | |
| 6,488,197 | B1 * | 12/2002 | Whitman | 227/180.1 |
| 6,506,202 | B1 | 1/2003 | Dutta et al. | |
| 6,666,854 | B1 | 12/2003 | Lange | |
| 6,667,825 | B2 | 12/2003 | Lu et al. | |
| 6,715,259 | B2 | 4/2004 | Johnston et al. | |
| 6,755,338 | B2 * | 6/2004 | Hahnen et al. | 227/175.1 |
| 6,756,094 | B1 | 6/2004 | Wang et al. | |
| 6,786,382 | B1 | 9/2004 | Hoffman | |
| 6,830,174 | B2 | 12/2004 | Hillstead et al. | |
| 6,905,057 | B2 | 6/2005 | Swayze et al. | |
| 6,951,675 | B2 | 10/2005 | Chin et al. | |
| 6,953,139 | B2 | 10/2005 | Milliman et al. | |
| 6,978,921 | B2 | 12/2005 | Shelton | |
| 7,087,052 | B2 * | 8/2006 | Sampson et al. | 606/41 |
| 7,111,769 | B2 | 9/2006 | Wales | |
| 7,112,357 | B2 | 9/2006 | Miller et al. | |
| 7,166,077 | B2 | 1/2007 | Millay et al. | |
| 7,213,736 | B2 | 5/2007 | Wales et al. | |
| 7,407,074 | B2 | 8/2008 | Ortiz et al. | |
| 7,410,086 | B2 | 8/2008 | Ortiz et al. | |
| 2003/0045900 | A1 | 3/2003 | Hahnen | |
| 2003/0111507 | A1 * | 6/2003 | Nunez | 227/180.1 |
| 2003/0178848 | A1 | 9/2003 | Williams | |
| 2004/0002726 | A1 | 1/2004 | Nunez et al. | |
| 2004/0108357 | A1 | 6/2004 | Milliman et al. | |
| 2004/0173659 | A1 | 9/2004 | Green et al. | |
| 2004/0179244 | A1 | 9/2004 | Taitun | |
| 2004/0232196 | A1 | 11/2004 | Shelton et al. | |
| 2004/0232197 | A1 | 11/2004 | Shelton et al. | |
| 2004/0232201 | A1 | 11/2004 | Wenchell et al. | |
| 2004/0243176 | A1 * | 12/2004 | Hahnen et al. | 606/205 |
| 2005/0006429 | A1 | 1/2005 | Wales et al. | |
| 2005/0006430 | A1 | 1/2005 | Wales | |
| 2005/0006432 | A1 * | 1/2005 | Racenet et al. | |
| 2005/0006434 | A1 | 1/2005 | Wales et al. | |
| 2005/0070958 | A1 | 3/2005 | Swayze et al. | |
| 2005/0107824 | A1 | 5/2005 | Hillstead et al. | |
| 2005/0165415 | A1 | 7/2005 | Wales | |
| 2005/0263562 | A1 | 12/2005 | Shelton | |
| 2006/0011699 | A1 | 1/2006 | Olson et al. | |
| 2006/0016853 | A1 | 1/2006 | Racenet | |
| 2006/0022014 | A1 | 2/2006 | Shelton, IV et al. | |
| 2006/0022015 | A1 * | 2/2006 | Shelton et al. | 227/176.1 |
| 2006/0025809 | A1 | 2/2006 | Shelton, IV | |
| 2006/0025813 | A1 * | 2/2006 | Shelton et al. | 606/205 |
| 2006/0025817 | A1 * | 2/2006 | Ortiz et al. | 606/219 |
| 2006/0041273 | A1 * | 2/2006 | Ortiz et al. | 606/205 |
| 2006/0047307 | A1 * | 3/2006 | Ortiz et al. | 606/219 |
| 2006/0047308 | A1 * | 3/2006 | Ortiz et al. | 606/219 |
| 2006/0089535 | A1 | 4/2006 | Raz et al. | |
| 2006/0190028 | A1 | 8/2006 | Wales | |
| 2006/0190032 | A1 * | 8/2006 | Wales | 606/205 |
| 2006/0226196 | A1 | 10/2006 | Hueil et al. | |
| 2006/0229665 | A1 | 10/2006 | Wales et al. | |
| 2006/0289600 | A1 | 12/2006 | Wales et al. | |
| 2007/0027468 | A1 | 2/2007 | Wales et al. | |

FOREIGN PATENT DOCUMENTS

| | | | |
|---|---|---|---|
| EP | 0 598 976 | * | 6/1994 |
| EP | 0717959 | | 6/1996 |
| EP | 0769273 | | 4/1997 |
| EP | 0807409 | | 11/1997 |
| EP | 0 603 472 | | 6/2004 |
| EP | 1495726 | | 1/2005 |
| EP | 1627605 | | 2/2006 |
| EP | 1693008 | | 8/2006 |
| WO | WO 01/93766 | | 12/2001 |
| WO | WO 03/013374 | | 2/2003 |
| WO | WO 03/101313 | | 12/2003 |
| WO | WO 2004/002327 | | 1/2004 |
| WO | WO 2004/006980 | | 1/2004 |
| WO | WO 2004/032762 | * | 4/2004 |
| WO | WO 2004/112618 | | 12/2004 |

OTHER PUBLICATIONS

EPO Search Report, Application No. 06250869.2, Jul. 13, 2006, pp. 1-4.

Australian Search Report for Application No. SG 200600909-6, dated Mar. 2, 2007.

Australian Search Report for Application No. SG 200601987-1, dated Feb. 8, 2007.

Danish Search Report for Application No. 200601986-3, dated Apr. 11, 2007.

European Search Report dated Jun. 19, 2006 for EPO Application No. 06250869.

European Search Report dated Aug. 8, 2007 for EPO Application No. 06251959.

European Search Report dated Jul. 19, 2007 for EPO Application No. 06253226.

European Search Report dated Aug. 21, 2007 for EPO Application No. 06254005.

European Search Report dated Nov. 23, 2007 for EPO Application No. 06253224.

Notice of Allowance dated Nov. 15, 2006 for U.S. Appl. No. 11/100,847.

Notice of Allowance dated Oct. 5, 2007 for U.S. Appl. No. 11/061,908.

Notice of Allowance dated Nov. 30, 2007 for U.S. Appl. No. 11/100,847.

Office Action dated Jun. 1, 2006 for U.S. Appl. No. 11/100,847.

Office Action dated Dec. 6, 2006 for U.S. Appl. No. 11/061,908.

Office Action dated Mar. 9, 2007 for U.S. Appl. No. 11/061,908.

Office Action dated Mar. 29, 2007 for U.S. Appl. No. 11/165,094.

Office Action dated Apr. 5, 2007 for U.S. Appl. No. 11/239,528.

Office Action dated Jun. 26, 2007 for U.S. Appl. No. 11/239,528.

Office Action dated Aug. 1, 2007 for U.S. Appl. No. 11/100,847.

Office Action dated Aug. 23, 2007 for U.S. Appl. No. 11/165,094.
Office Action dated Sep. 7, 2007 for U.S. Appl. No. 11/238,358.
Office Action dated Jan. 14, 2008 for U.S. Appl. No. 11/239,528.
Notice of Allowance dated Oct. 5, 2007 for U.S. Appl. No. 11/061,908.
Notice of Allowance dated Nov. 16, 2007 for U.S. Appl. No. 11/061,908.
Notice of Allowance dated Feb. 20, 2008 for U.S. Appl. No. 11/061,908.
Notice of Allowance dated Jul. 31, 2008 for U.S. Appl. No. 11/238,358.
Final Rejection dated Mar. 26, 2008 for U.S. Appl. No. 11/238,358.
Non-Final Rejection dated Apr. 7, 2008 for U.S. Appl. No. 1/165,468.
Non-Final Rejection dated Jul. 11, 2008 for U.S. Appl. No. 11/239,528.
Non-Final Rejection dated Jul. 17, 2008 for U.S. Appl. No. 11/100,772.
European Search Report dated Nov. 20, 2006 for Application No. 06254005.
European Search Report dated Nov. 23, 2007 for Application No. 06253224.
EPO Search Report dated Jul. 28, 2006 for Application No. 06253224.*
EPO Search Report dated Aug. 31, 2006 for Application No. 06253226.*
EPO Search Report dated Nov. 20, 2006 for Application No. 06254005.*
EPO Search Report dated May 5, 2008 for Application No. 06251960.*

* cited by examiner

SURGICAL INSTRUMENT HAVING FLUID ACTUATED OPPOSING JAWS

CROSS REFERENCE TO RELATED APPLICATIONS

This application is a continuation-in-part of commonly owned U.S. patent application Ser. No. 11/061,908 entitled “SURGICAL INSTRUMENT INCORPORATING A FLUID TRANSFER CONTROLLED ARTICULATION MECHANISM” to Kenneth Wales and Chad Boudreaux, filed on Feb. 18, 2005, now abandoned, the disclosure of which is hereby incorporated by reference in its entirety.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments.

BACKGROUND OF THE INVENTION

Surgical instruments for minimally invasive surgery are increasingly relied upon to reduce the hospital stay and recovery time for various surgical procedures. Many of these surgical instruments include mechanisms that actuate an end effector via an elongate shaft that performs a surgical step that entails two opposing surfaces being brought into opposition to each other. For instance, pivotally opposed jaws are used in graspers. Pivotally attached scissor blades are incorporated into cutting devices. Providing an actuating control down the elongate shaft with sufficient strength is complicated by a design goal of minimum cross sectional area so as to pass through a small cannula of a trocar. In addition, the elongate shaft often has a plurality of control functions (e.g., rotation, articulation, etc.) Further, it is desirable to have reduced design complexity so as to provide an economical device.

As an illustration of a particularly challenging surgical instrument, surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications, described in U.S. Pat. No. 5,465,895, advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

These minimally invasive surgical instruments have been widely used and have proven to be a significant advance over traditional open surgical techniques. It would be desirable to incorporate yet additional features and capabilities.

BRIEF SUMMARY OF THE INVENTION

The invention overcomes the above-noted and other deficiencies of the prior art by including a surgical instrument that is suitable for minimally invasive surgical procedures which has a handle that positions an end effector through a surgical opening via an elongate shaft. The end effector has a pair of pivoting members opposingly contacting tissue. A fluid actuated closure mechanism responds to a closure action by a fluid actuator attached to the handle by bi-directionally transferring fluid across a fluid conduit to a fluid reservoir positioned to urge the pair of pivoting members closed. Thereby, the integration of fluid conduits within an elongate shaft allows for shafts of a desirable small cross section which are able to perform an important surgical operation.

In one aspect of the invention, a surgical instrument has an end effector that is actuated by a fluid actuator to open and close upon tissue. Once closed, a firing bar that is received for reciprocating a longitudinal firing motion in an elongate shaft transfers a longitudinal firing motion from a handle to actuate a staple cartridge and to sever the clamped tissue in the end effector.

In yet another aspect of the invention, a surgical instrument includes a handle that produces closure actuation that transfers fluid through a fluid conduit in an elongate shaft to a fluid actuator positioned in a lever cavity to position a lever. The lever of a first tissue contacting member extends proximally into the lever cavity from a pivotal connection with a second tissue contacting member. Fluid transfer advantageously effects pivotal movement of the pair of tissue contacting members.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
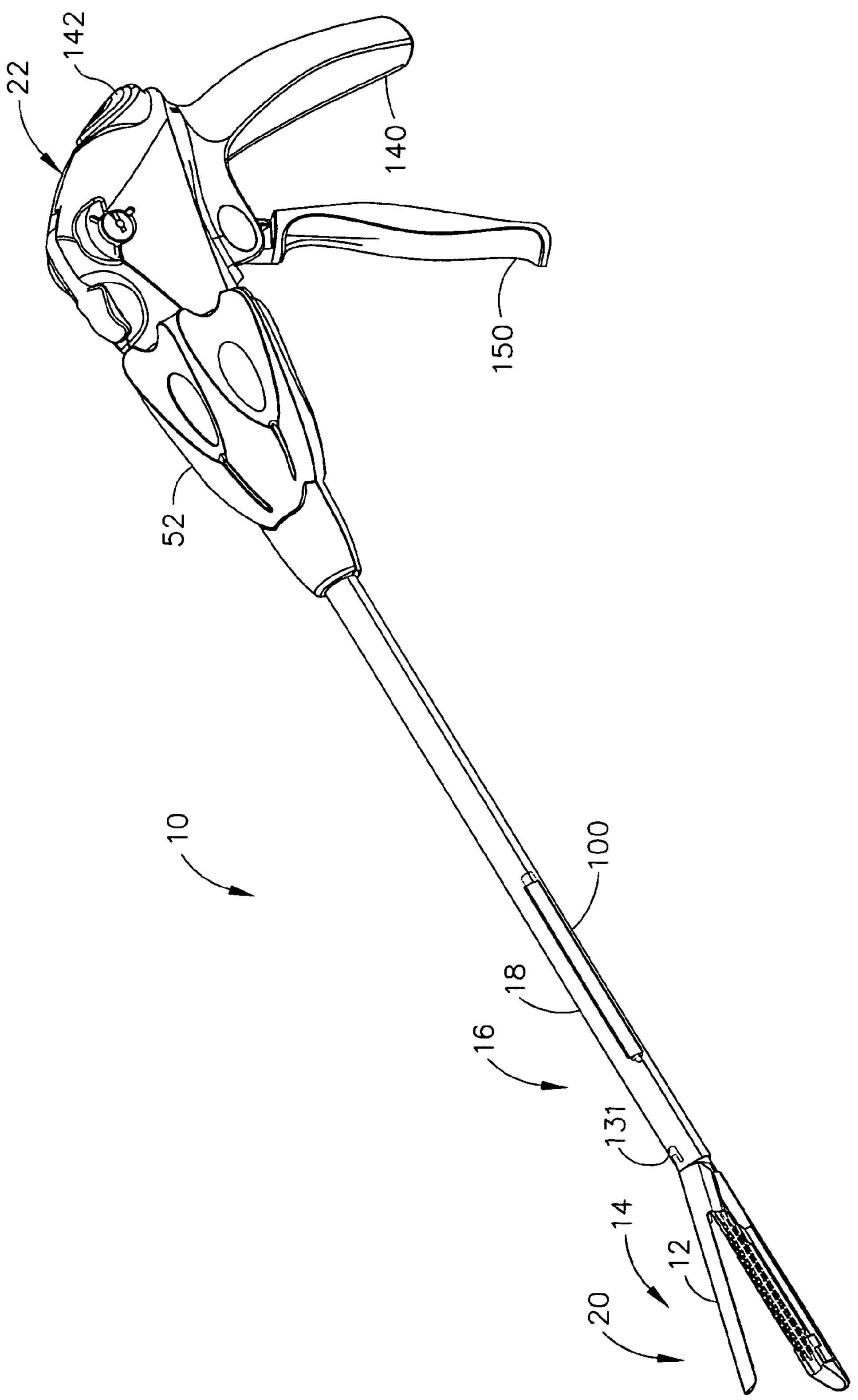
FIG. 1 is a perspective view of a surgical stapling and severing instrument having a fluid actuated upper jaw (anvil) in an open position and an electroactive polymer (EAP) medical substance dispensing shaft.
Figure 2:
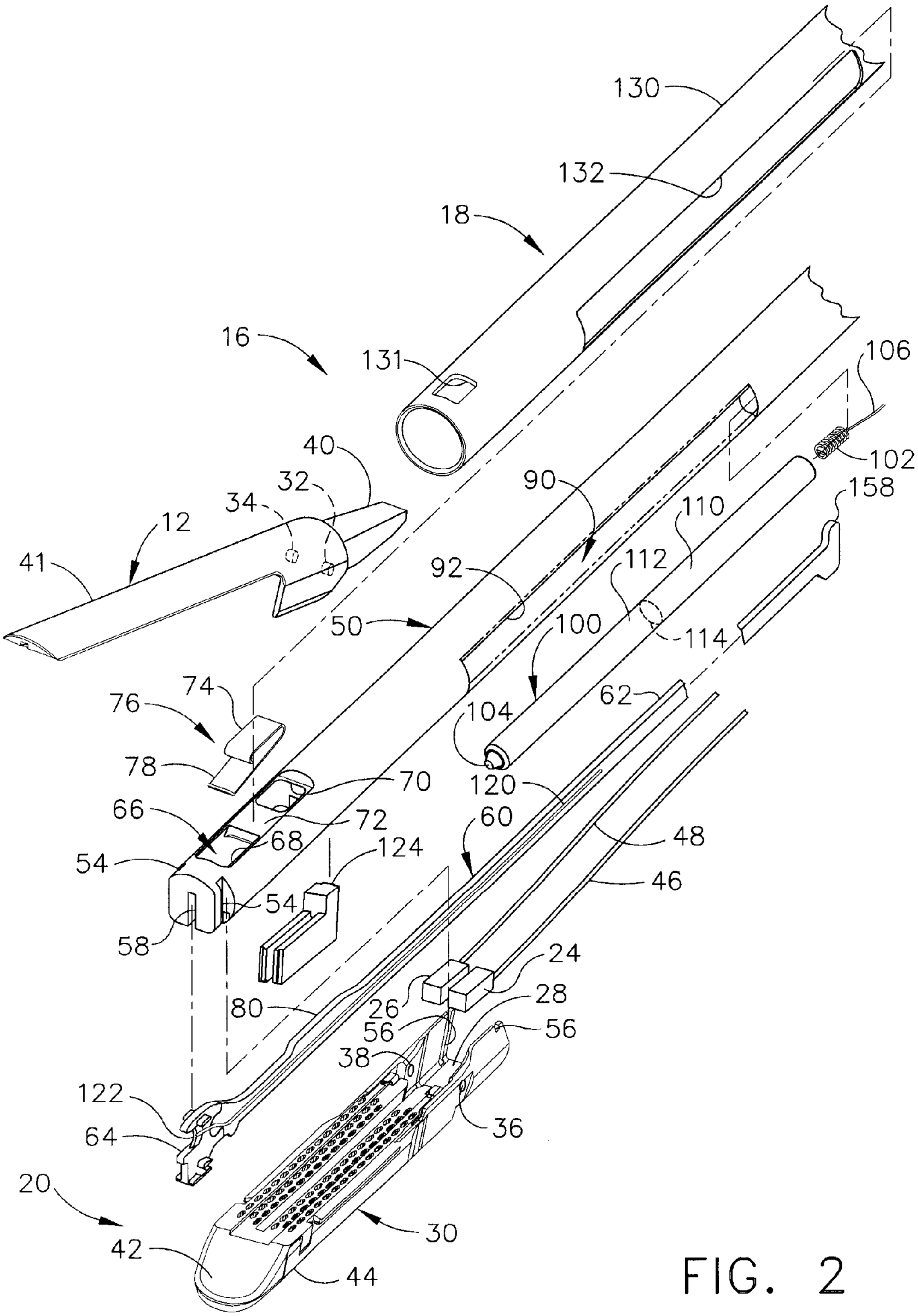
FIG. 2 is a disassembled perspective view of an implement portion of the surgical stapling and severing instrument of FIG. 1.

Turning to the Drawings, wherein like numerals denote like components throughout the several views, FIGS. 1-2 show a surgical stapling and severing instrument 10 that is capable of practicing the unique benefits of the present invention, including both fluid actuation (e.g., opening, closing/clamping) of an upper jaw (anvil) 12 of an end effector 14 as well as dispensing a medical substance onto tissue as severed. Fluid actuation of the end effector 14 provides a range of design options that avoid some design limitations of traditional mechanical linkages. For example, instances of binding or component failure may be avoided. Further, dispensing liquids onto severed tissue allows for a range of advantageous therapeutic treatments to be applied, such as the application of anesthetics, adhesives, cauterizing substances, antibiotics, coagulant, etc.

With particular reference to FIG. 2, the surgical stapling and severing instrument 10 includes an implement portion 16 formed by an elongate shaft 18 and an end effector 14, depicted as a stapling assembly 20. The surgical stapling and severing instrument 10 also includes a handle 22 (FIG. 1) attached proximally to the shaft 18. The handle 22 remains external to the patient as the implement portion 16 is inserted through a surgical opening, or especially a cannula of a trocar that forms a pneumoperitoneum for performing a minimally invasive surgical procedure.

Left and right fluid actuator bladders (lift bags) 24, 26 are supported within an aft portion 28 of a staple channel 30. The anvil 12 includes a pair of inwardly directed lateral pivot pins 32, 34 that pivotally engage outwardly open lateral pivot recesses 36, 38 formed in the staple channel 30 distal to the aft portion 28. The anvil 12 includes a proximally directed lever tray 40 that projects into the aft portion 28 of the staple channel 30 overtop and in contact with the fluid actuator bladders (lift bags) 24, 26 such that filling the fluid actuator bladders 24, 26 causes a distal clamping section 41 of the anvil 12 to pivot like a teeter-totter toward a staple cartridge 42 held in an distal portion 44 of the staple channel 30. Evacuation and collapse of the fluid actuator bladders 24, 26, or some other resilient feature of the end effector 14, causes the anvil 12 to open. Left and right fluid conduits 46, 48 communicate respectively with the left and right fluid actuator bladders 24, 26 to bi-directionally transfer fluid for actuation.

It will be appreciated that the terms "proximal" and "distal" are used herein with reference to a clinician gripping a handle of an instrument. Thus, the staple applying assembly 20 is distal with respect to the more proximal handle 22. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

The elongate shaft 18 includes a frame 50 (FIG. 2) whose proximal end is rotatably engaged to the handle 22 such that a rotation knob 52 rotates the frame 50 along with the end effector 14. A distal end of the frame has lateral recesses 54 that engage a distal lip 56 of the staple channel 30. The frame 50 includes a laterally centered, bottom firing slot 58 that passes longitudinally through the frame 50 for receiving a two-piece firing bar 60 comprised of a firing bar 62 with a distally attached E-beam 64, the latter translating within the staple applying assembly 20 to sever and staple tissue. A distal portion of the frame 50 includes an upper cavity 66 whose distal and proximal ends communicate through distal and proximal apertures 68, 70, defining there between a cross bar 72 over which a distally projecting clip 74 of a clip spring 76 engages with a lower spring arm 78, distally and downwardly projecting through the upper cavity 66 to bias the firing bar 62 downwardly into engagement with the staple channel 30, especially when the lower spring arm 78 encounters a raised portion 80 on the firing bar 62.

Medical substance dispensing is integrated into the elongate shaft 18 by including a laterally offset cylindrical cavity 90 formed in the frame 50 that communicates along its longitudinal length to the outside via a rectangular aperture 92 that is slightly shorter than an electroactive polymer (EAP) syringe 100 that is inserted through the aperture 92 into the cylindrical cavity 90. A proximal portion of the cylindrical cavity 90 contains a longitudinally aligned compression spring 102 that urges a distal dispensing cone 104 of the EAP syringe 100 distally into sealing contact with the frame 50 and allows translation for insertion and removal of the EAP syringe 100. An electrical conductor 106 passes through the frame 50 and is attached to the compression spring 102, which is also formed of an electrically conductive metal. An aft portion of the EAP syringe is conductive and contacts the spring 102 to form a cathode to an EAP actuator 110 held in a proximal portion of the EAP syringe 100. It will be appreciated that another conductor, perhaps traveling with the conductor 106, also electrically communicates to the EAP actuator 110 to serve as the anode.

When activated, the EAP actuator 110 longitudinally expands, serving as a plunger to dispel a medical substance 112 in a distal portion of the EAP syringe 100 through the distal dispensing cone 104. Insofar as the EAP actuator 110 laterally contracts to compensate for its longitudinal expansion, a plunger seal 114 maintains a transverse seal within the EAP syringe 100. A vent (not shown), such as around conductor 106 allows air to refill the EAP syringe 100 as the medical substance 112 is dispensed. The vent may rely upon the surface tension of the medical substance 112 to prevent leaking. Alternatively, a one-way valve may be used for the same purpose. As described below, the medical substance 112 is conducted by the frame 50 to a lateral fluid groove 120 that is formed in the firing bar 62 and the E-beam 64 to direct the medical substance to a cutting surface 122 of the E-beam 64. The frame slot 58 is sized to seal the lateral fluid groove 120. The portion of the lateral fluid groove 120 that is positioned under the spring clip 76 is sealed by a firing bar guide 124. In the illustrative version, an outer sheath 130 encompasses the frame 50 and proximally projecting lever tray 40 of the anvil 12. A top distal opening 131 allows closing of the anvil 12.

An outer rectangular aperture 132 of the outer sheath 130 is sized and longitudinally positioned to correspond to the rectangular aperture 92 formed in the frame 50. In some applications, the outer sheath 130 may be rotated to selectively align the rectangular aperture 92 with the outer rectangular aperture 132 for insertion or removal of the EAP syringe 100. It should be appreciated that in some applications the EAP syringe 100 may be integrally assembled into an elongate shaft that does not allow for selecting a desired medical substance. For instance, a disposable implement portion with an integral staple cartridge and medical dispensing reservoir may be selected by the clinician as a unit. It is believed that allowing insertion at the time of use, though, has certain advantages including clinical flexibility in selecting a medical substance (e.g., anesthetics, adhesives, antibiotics, cauterizing compound, etc.) and extending the shelf life/simplifying storage and packaging of the implement portion 16.

In the illustrative version, an elongate stack of many disk-shaped EAP layers are aligned longitudinally and configured to expand along this longitudinal axis. Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30-50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material, manufactured by Santa Fe Science and Technology and sold as PANION™ fiber, is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is manufactured by Artificial Muscle Inc, a division of SRI Laboratories. Plate EAP material is manufactured by EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands, flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2-4% where the typical laminate version achieves 20-30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers there between to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Additional description of applications of EAP actuators in a surgical instrument are described in commonly-owned U.S. patent application Ser. No. 11/082,495 filed on 17 Mar. 2005, and entitled "SURGICAL INSTRUMENT INCORPORATING AN ELECTRICALLY ACTUATED ARTICULATION MECHANISM", the disclosure of which is hereby incorporated by reference in its entirety.

Returning to FIG. 1, the handle 22 controls closure of the anvil 12, firing of the two-piece firing bar 60, and dispensing of the medical substance. In an illustrative version, a pistol grip 140 may be grasped and a thumb button 142 depressed as desired to control closure of the anvil 12. The thumb button 142 provides a proportional electrical signal to an EAP dispensing actuator (not shown) similar to the EAP syringe 100 to transfer fluid through the conduits 46, 48 to the fluid actuator bladders 24, 26 to close the anvil 12 (FIG. 2). When the thumb button 142 is fully depressed, a mechanical toggle lock (not shown) engages to hold the thumb button 142 down until a full depression releases the toggle lock for releasing the thumb button 142. Thus, when the thumb button 142 is held down, the surgeon has a visual indication that the end effector 14 is closed and clamped, and they may be maintained in this position by continued activation of an EAP dispensing actuator or by a locking feature. For instance, control circuitry may sense movement of the thumb button 142, causing a normally closed EAP shutoff valve (not shown) to open that communicates between the EAP dispensing actuator and the conduits 46, 48. Once movement ceases, the EAP shutoff valve is allowed to close again, maintaining the anvil 12 position. In addition, a manual release could be incorporated to defeat such a lockout to open the anvil 12.

Figure 22:
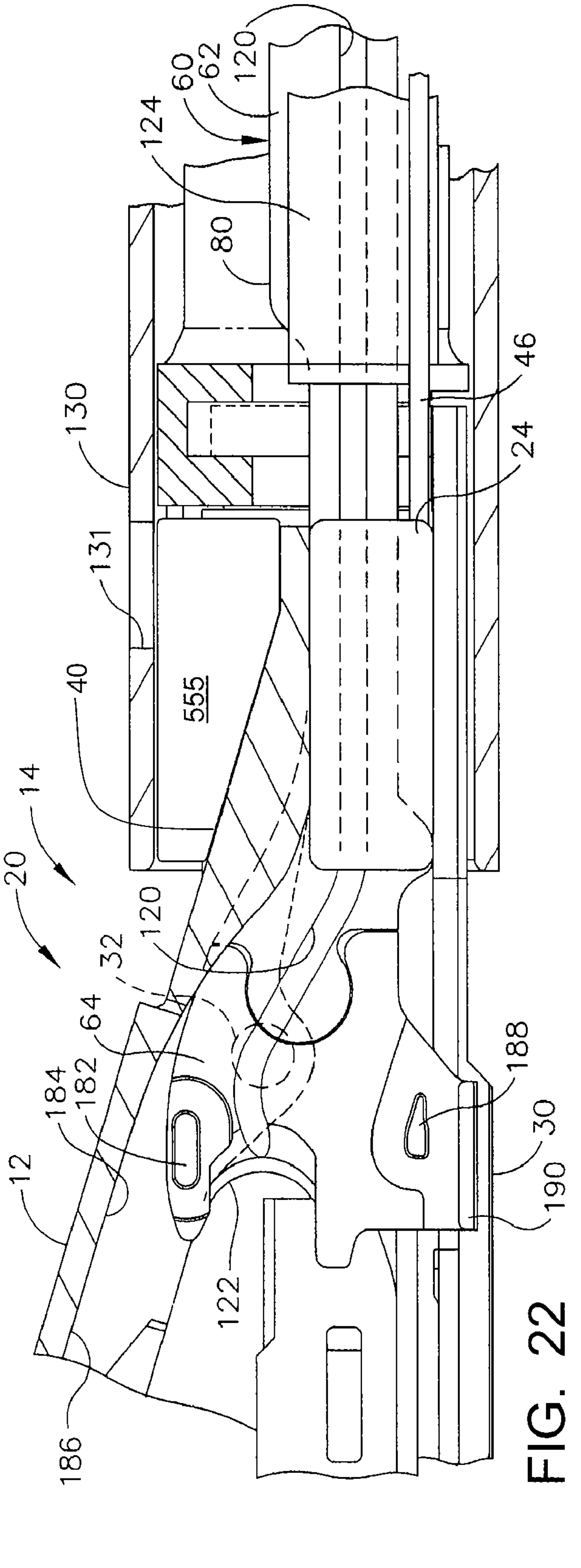
FIG. 22 is a cross sectional left side view of a portion of the instrument of FIG. 4 with an opposing lifting bag.

As an alternative, a closure trigger (not shown) or other actuator may be included that bi-directionally transfers fluid to the fluid actuator bladders 24, 26. In the above-referenced patent application Ser. No. 11/061,908, a number of such fluid actuators for articulation of a pivoting shaft are described that may be adapted for closing the anvil 12. To take full advantage of the differential fluid transfer described for several of these versions, it should be appreciated that an opposing lift bag 555 as shown in FIG. 22 may be placed above the lever tray 40 of the anvil 12 to assert an opening force as the left and right fluid actuator bladders (lift bags) 24, 26 collapse.

To avoid undesirable firing situations, sensing may be advantageously incorporated into the control circuitry. For instance, a pressure transducer and/or position sensing may be positioned to monitor the fluid transfer and/or anvil position. For instance, the proximity of the anvil to the 12 to the staple channel 30 may be sensed and firing locked out if not closed. Monitoring may detect a fluid pressure exceeding a threshold indicating that anvil 12 commanded closed with something preventing this closing (e.g., excessive tissue in the end effector 14). Similarly, a fluid pressure below a lower threshold with anvil 12 commanded open may indicate an inability for the anvil 12 to open (e.g., abutting tissue). Colored light emitting diodes (LEDs) (not shown) on the handle 22 may give an indication to the surgeon by color, flashing, etc. These indications may include POWER ON, Self-Test GOOD, Self-Test BAD, BATTERY LOW, ANVIL OPEN, ANVIL CLOSED, ANVIL BLOCKED OPEN, ANVIL BLOCK CLOSED. An indication that would warrant precluding firing may be used to disable firing.

Figure 3:
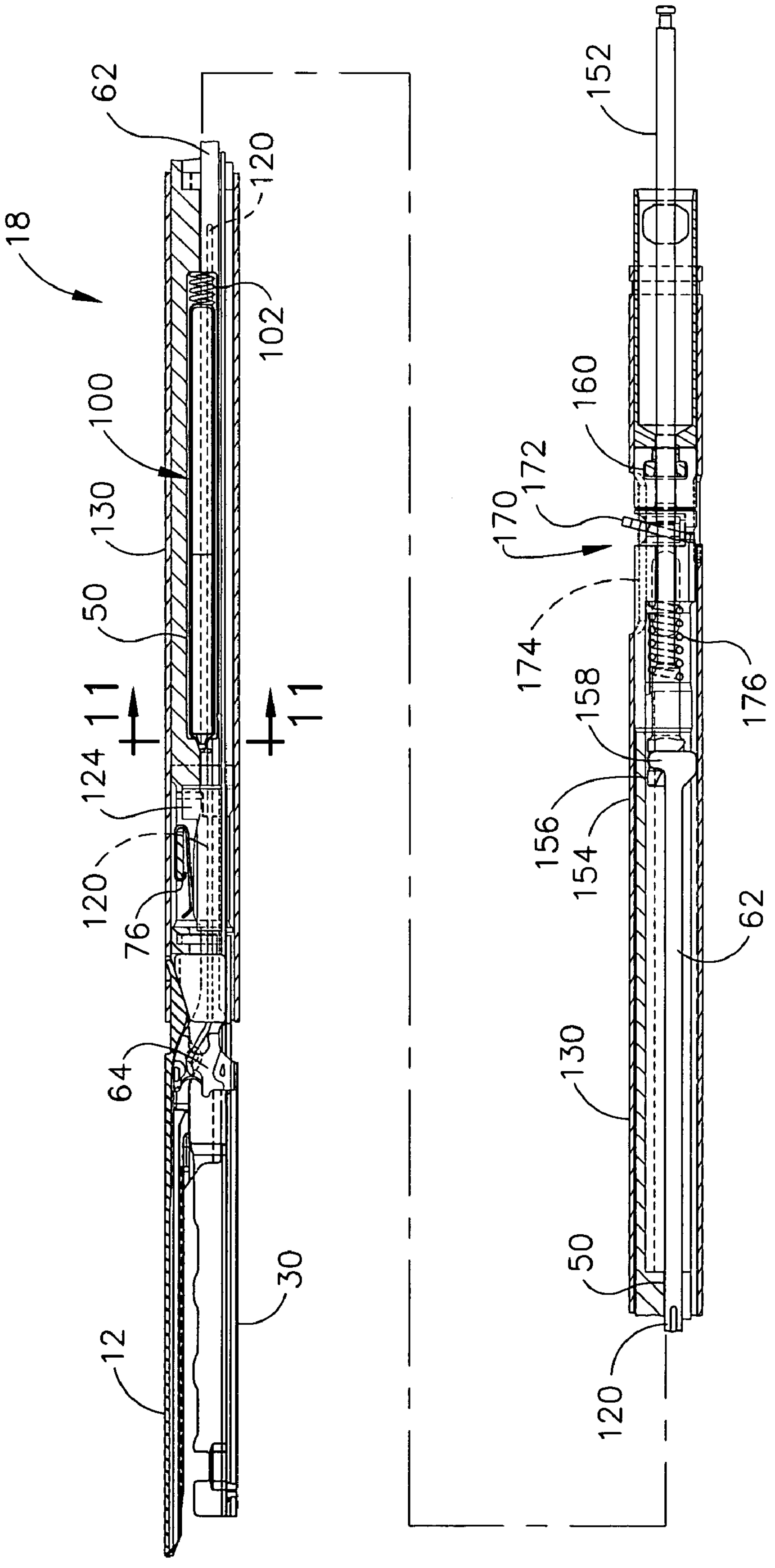
FIG. 3 is left side view in a elevation of the implement portion of the surgical stapling and severing instrument of FIG. 1 taken in cross section generally through a longitudinal axis and passing through an offset EAP syringe and receptacle that is in fluid communication with a dispensing groove in an E-beam firing bar.

With particular reference to FIG. 3, the handle 22 includes a firing trigger 150 (FIG. 1) that is drawn proximally toward the pistol grip 140 to cause a firing rod 152 to move distally in a proximal portion 154 of the elongate shaft 18. A distal bracket 156 of the firing rod 152 engages an upward proximal hook 158 of the firing bar 62. A dynamic seal 160 within the frame 50 seals to the firing rod 152 so that the implement portion is pneumatically sealed when inserted into an insufflated abdomen.

An anti-backup mechanism 170 of the firing rod 152 may be advantageously included for a handle 22 that includes a multiple stroke firing trigger 150 and a retraction biased firing mechanism coupled to the firing rod 152 (not shown). In particular, an anti-backup locking plate 172 has the firing rod 152 pass through a closely fitting through hole (not shown) that binds when a retracting firing rod 152 tips the lock plate 172 backward as shown with the bottom of the locking plate held in position within the frame 50. An anti-backup cam sleeve 174 is positioned distal to the anti-backup locking plate 172 and urged into contact by a more distal compression spring 176 through which the firing rod 152 passes and that is compressed within the frame 50. It should be appreciated that mechanisms in the handle 22 may manually release the anti-backup mechanism 170 for retraction of the firing rod 152.

Figure 4:
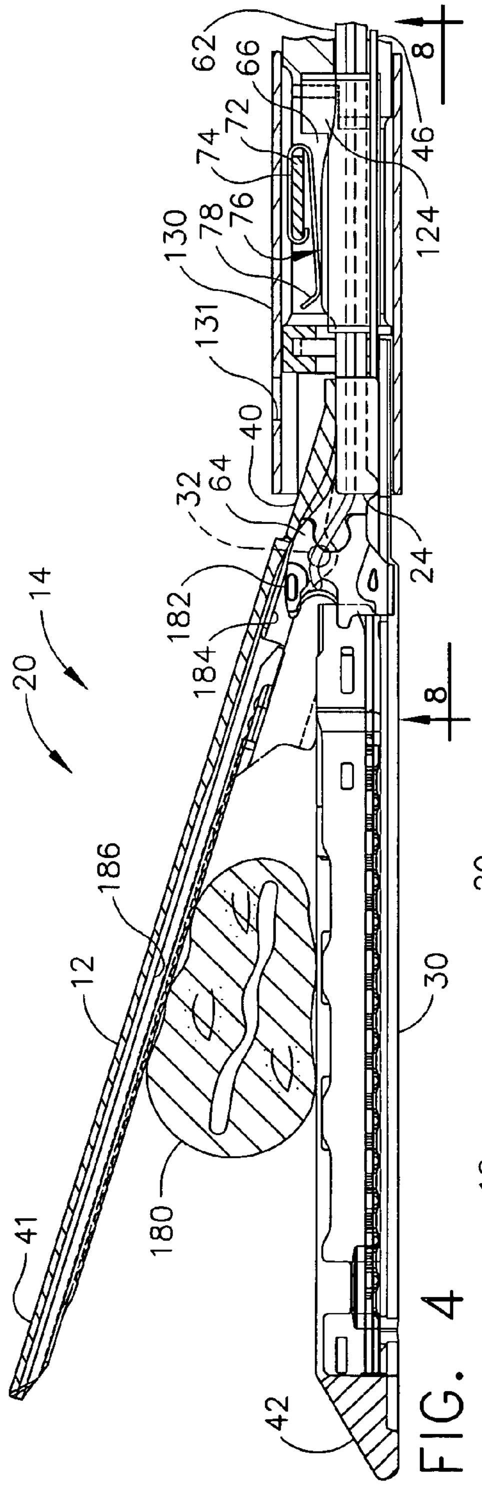
FIG. 4 is a left side detail view in elevation of a distal portion of the implement portion of the surgical stapling and severing instrument of FIG. 1 taken in cross section generally through the longitudinal axis thereof but showing a laterally offset fluid actuator bladder actuator opening the anvil.
Figure 5:
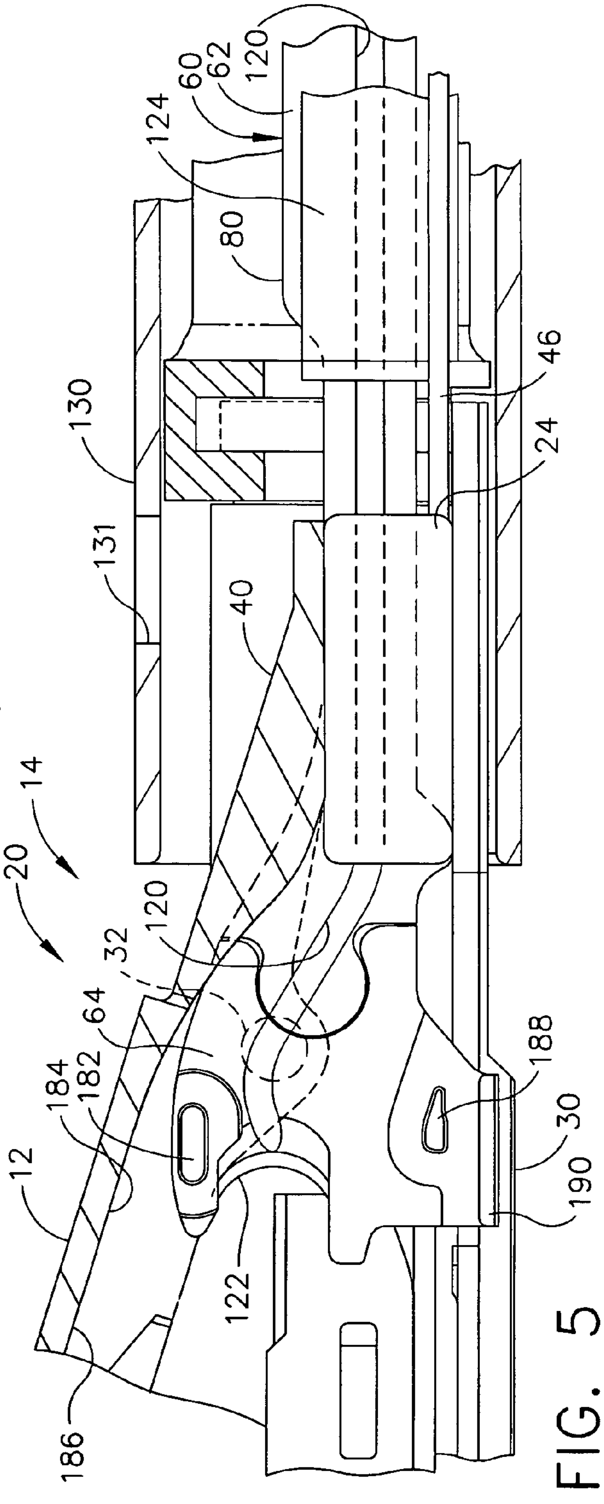
FIG. 5 is a left side detail view of an E-beam firing bar incorporating medical substance ducting.

In FIGS. 4-5, the end effector 14, which in the illustrative version is a staple applying assembly 20, is opened by having fluid actuator bladder 24 deflated, drawing down lever tray 40 of the anvil 12, which pivots about pin 32 raising distal clamping section 41 thereby allowing positioning body tissue 180 between the anvil 12 and staple cartridge 42. The E-beam 64 has an upper pin 182 that resides within an anvil pocket 184 allowing repeated opening and closing of the anvil 12. An anvil slot 186, formed along the length of the anvil 12, receives the upper pin 182 when the anvil 12 is closed and the two piece firing bar 60 is distally advanced. A middle pin 188 slides within the staple cartridge 42 above the staple channel 30 in opposition to a bottom pin or foot 190 that slides along a bottom surface of the staple channel 30.

Figure 6:
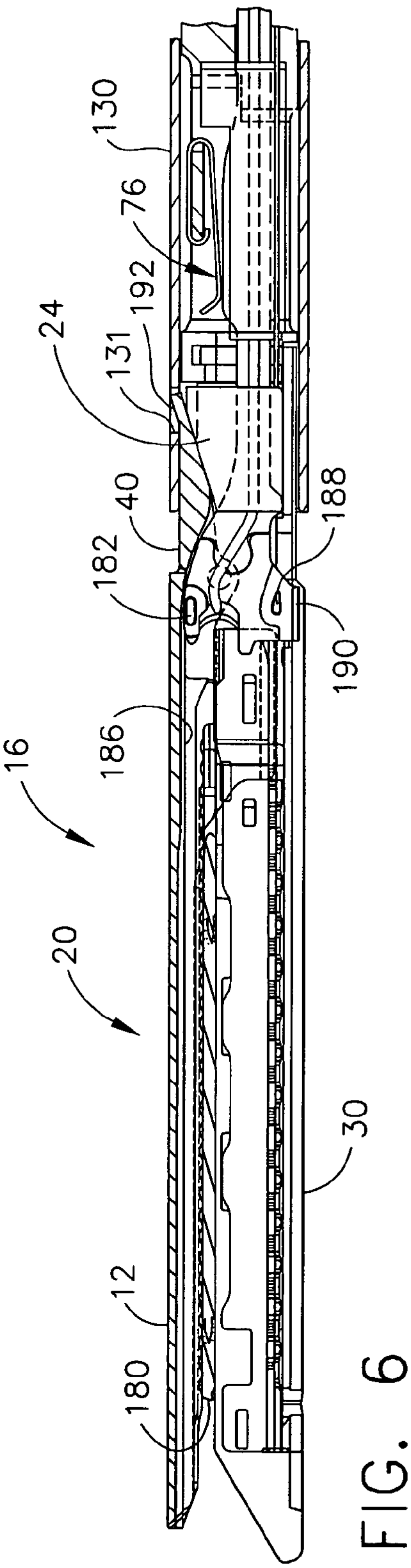
FIG. 6 is a left side detail view in elevation of the distal portion of the implement portion of the surgical stapling and severing instrument of FIG. 4 taken in cross section generally through the longitudinal axis thereof with the anvil closed.
Figure 7:
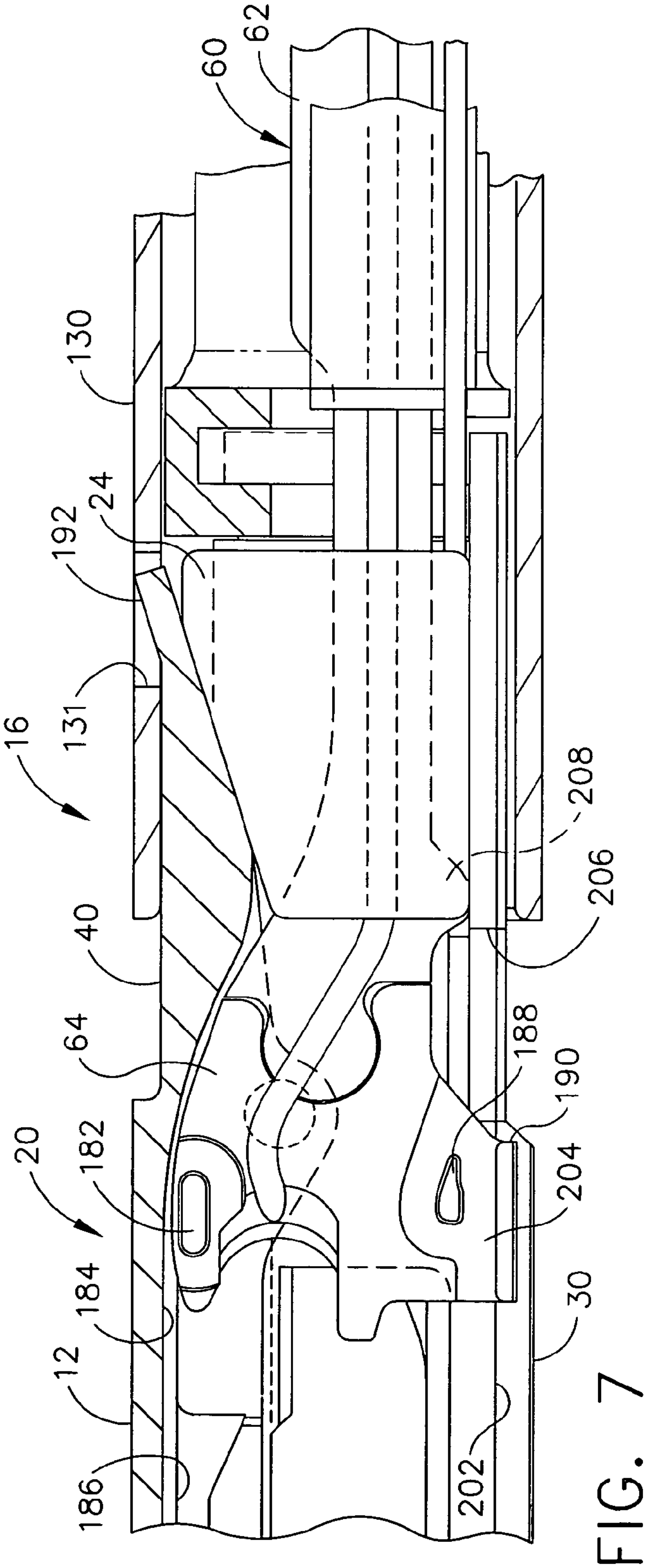
FIG. 7 is a left side detail view of the E-beam firing bar of FIG. 6.

In FIGS. 6-7, the staple applying assembly 20 has been closed by expanding the fluid actuator bladder (lift bag) 24, raising the lever tray 40 of the anvil 12 until flush with the outer sheath 130, with a proximal upwardly bent tip 192 of the lever tray 40 allowed to enter the top distal opening 131. This bent tip 192, in combination with the opening 131, advantageously allows greater radial travel for the anvil 12 as well as presenting an abutting surface rather than a piercing tip to the underlying fluid actuator bladder 24. When the anvil 12 is closed, the upper pin 182 is aligned with the anvil slot 186 for firing and the tissue 180 is flattened to a thickness appropriate for severing and stapling.

Figure 8:
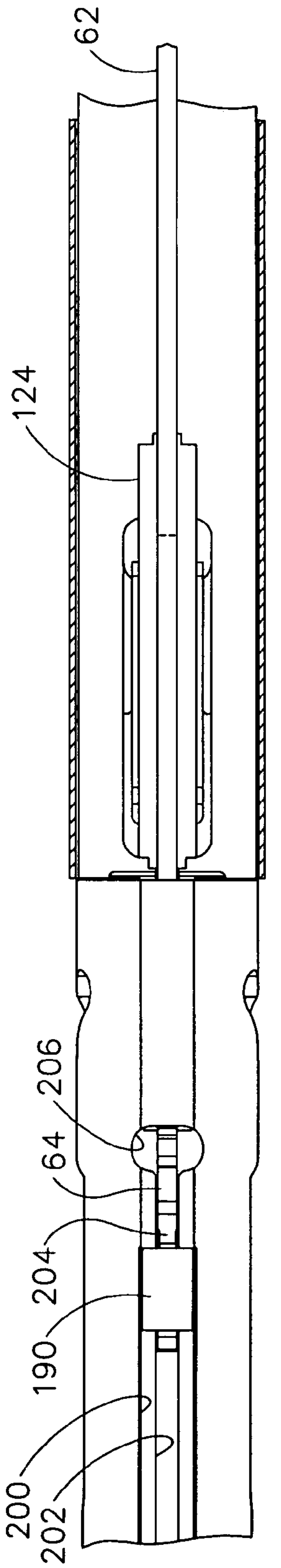
FIG. 8 is a top detail view of a joined portion of a lower jaw (staple channel) of the end effector and elongate shaft taken in cross section through the lines 8-8 depicting guidance to the E-beam firing bar.
Figure 9:
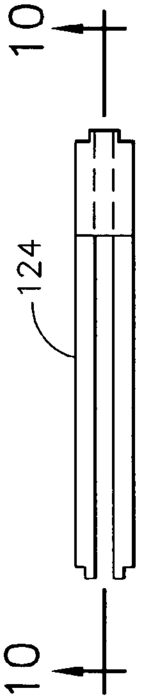
FIG. 9 is a front view of a firing bar guide of the implement portion of the surgical stapling and severing instrument of FIG. 2.
Figure 10:
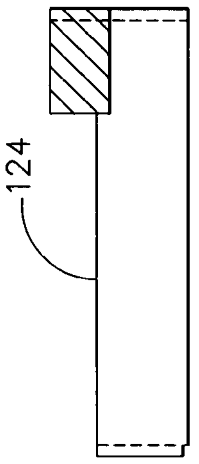
FIG. 10 is a left side view of the firing bar guide of FIG. 9 taken in cross section along lines 9-9.
Figure 11:
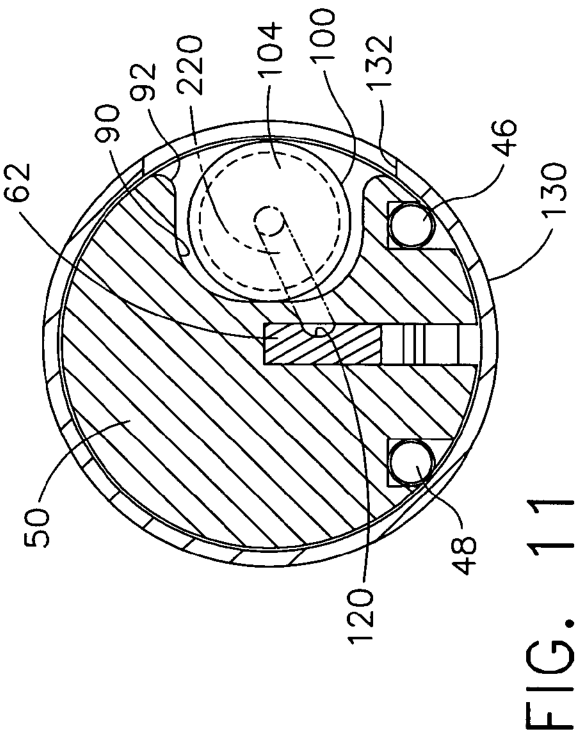
FIG. 11 is a front view in elevation of the elongate shaft of the surgical stapling and severing instrument of FIG. 3 taken along lines 11-11 taken through a distal end of the EAP medical substance syringe.
Figure 12:
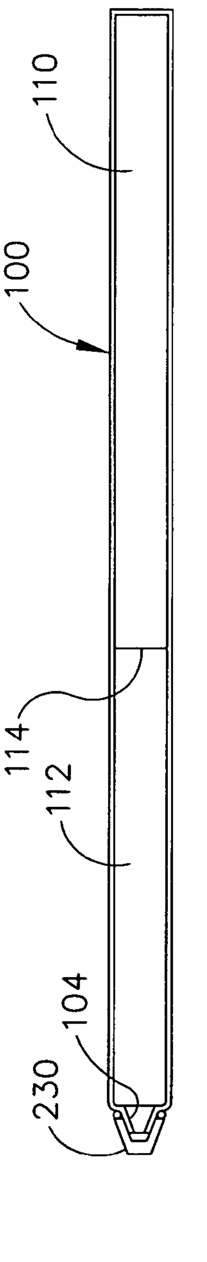
FIG. 12 is a left side view of the EAP medical substance syringe of FIG. 11.
Figure 13:
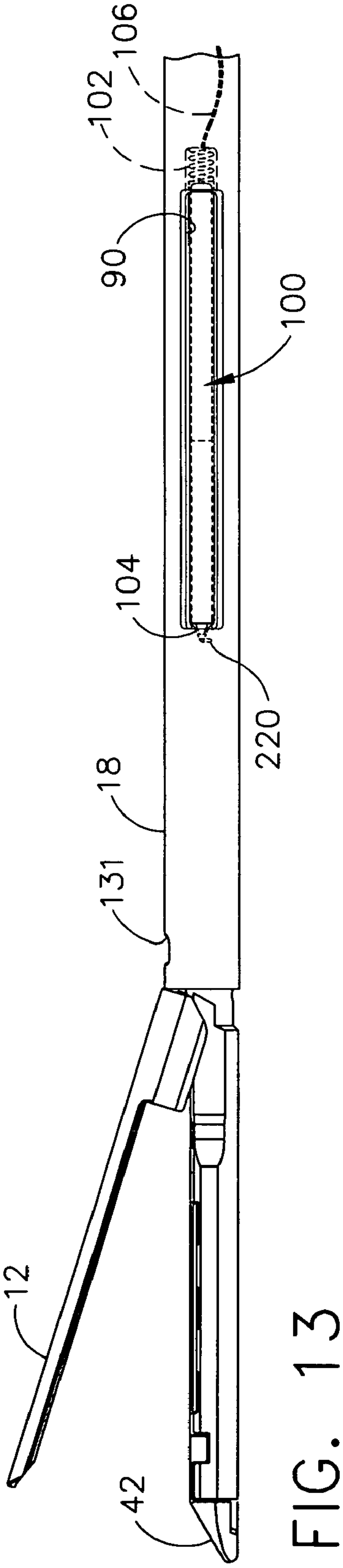
FIG. 13 is a left side view of the implement portion of the surgical stapling and severing instrument of FIG. 1 partially cut away to show proximal mountings for the EAP medical substance syringe.
Figure 14:
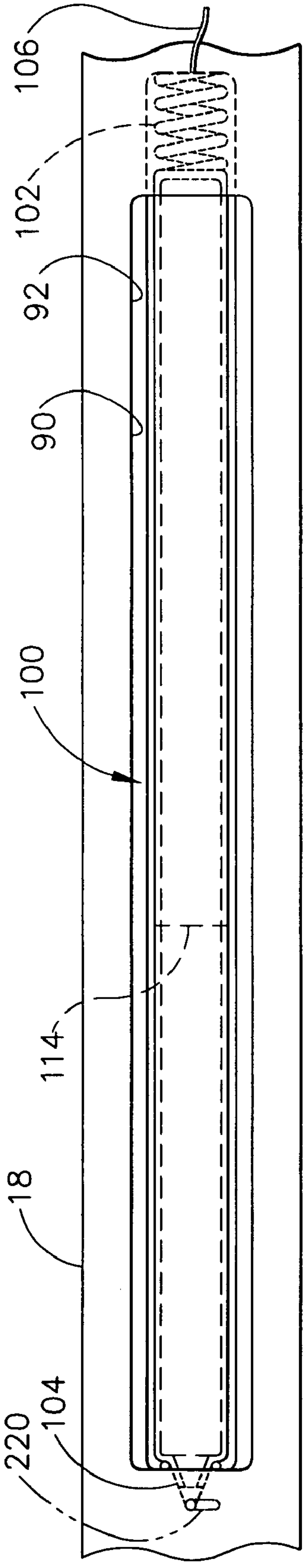
FIG. 14 is a left side detail view of the EAP medical substance syringe and receptacle of the elongate shaft of the surgical stapling and severing instrument of FIG. 13.
Figure 15:
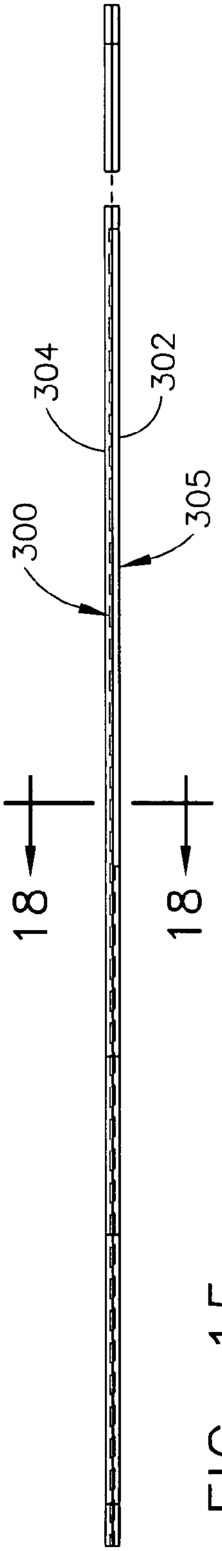
FIG. 15 is a top view of the firing bar of the surgical stapling and severing instrument of FIG. 2.
Figure 16:
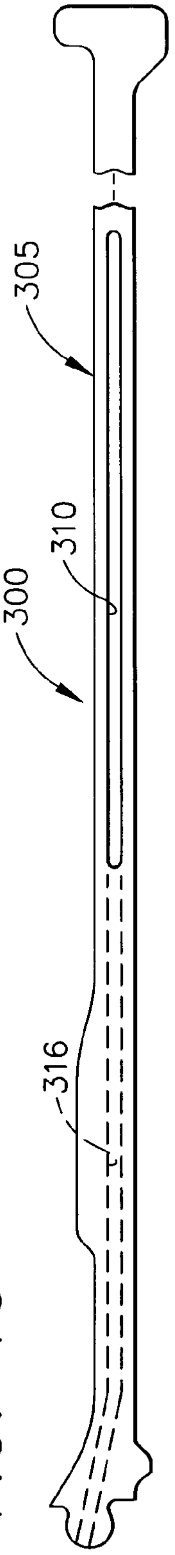
FIG. 16 is a left side view of a laminate firing bar showing an internal fluid path in phantom for the surgical stapling and severing instrument of FIG. 1.
Figure 18:
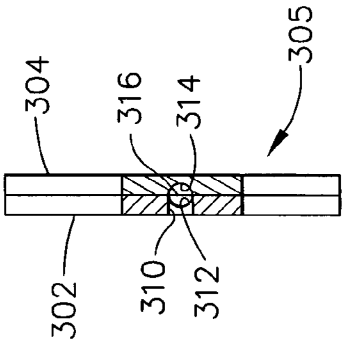
FIG. 18 is a front view in elevation of the laminate firing bar of FIG. 15 taken in cross section along line 18-18 through a proximal open groove of a fluid path.
Figure 17:
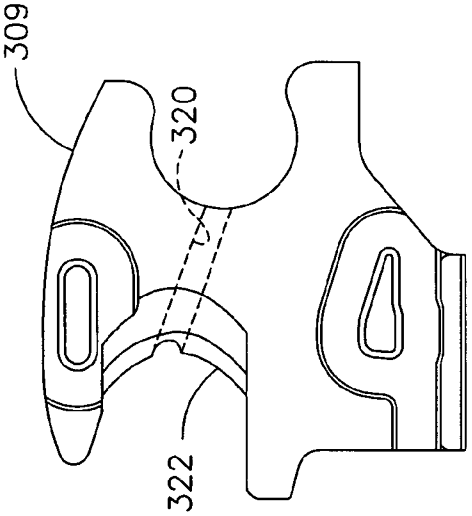
FIG. 17 is a left side detail view of an alternate E-beam showing an internal fluid path in phantom showing an internal fluid path in phantom.

In FIGS. 7-8, the E-beam 64 is cut away to show its bottom foot 190 riding along a downwardly open laterally widened recess 200 that communicates with a narrow longitudinal slot 202 through which a vertical portion 204 of the E-beam 64 passes. A proximal aperture 206 to the narrow longitudinal slot 202 allows an assembly entrance for the lower foot 190. A bottom bump 208 is positioned on the firing bar 62 to drop into the proximal aperture 206 during an initial portion of firing travel under the urging of the clip spring 76 against the upper portion 80 of the firing bar 62 for proper engagement and for possible interaction with an end effector firing lockout mechanism (not shown). Also, this position allows for the end effector 14 to be pinched shut to facilitate insertion through a surgical entry point such as a cannula of a trocar (not shown). With reference to FIGS. 8-10, the firing bar guide 124 laterally contacts a portion of the firing bar 62 to close the corresponding portion of the lateral fluid groove 120. In FIG. 11, the EAP syringe 100 in the cylindrical cavity 90 has its distal dispensing cone 104 communicating with a radial fluid passage 220 formed in the frame 50 that communicates in turn with the lateral fluid groove 120. In FIG. 12, before installation in the surgical stapling and severing instrument 10, the EAP syringe 100 may be advantageously sealed with a disposable cap 230. In FIGS. 13-14, the EAP syringe 100 is shown without the disposable cap 230 and urged by spring 230 distally to engage the distal dispensing cone 104 into communication with the radial fluid passage 220.

It should be appreciated that one or more sensor in the surgical stapling and severing instrument 10 may sense a firing condition (e.g., movement of firing bar or mechanism coupled to the firing bar, position of the firing trigger, a separate user control to dispense, etc.) and activate dispensing control circuitry to effect dispensing.

In FIGS. 15-18, an alternate two-piece firing bar 300 is formed from longitudinally laminated left half and right half firing bar portions 302, 304 that form a firing bar 305 attached to an E-beam 309. Thereby, fluid transfer down the firing bar 300 may be further constrained. In particular, a left side fluid groove 310 in the left half firing bar portion 302 transitions distally to a pair of aligned internal fluid grooves 312, 314 respectively in the left and right half firing bar portions 302, 304, defining an internal fluid passage 316. Since the E-beam 309 is laterally thicker and of short longitudinal length, a drilled fluid passage 320 is formed therein between a cutting surface 322 and an aft edge aligned to communicate with the internal fluid passage 316.

Figure 19:
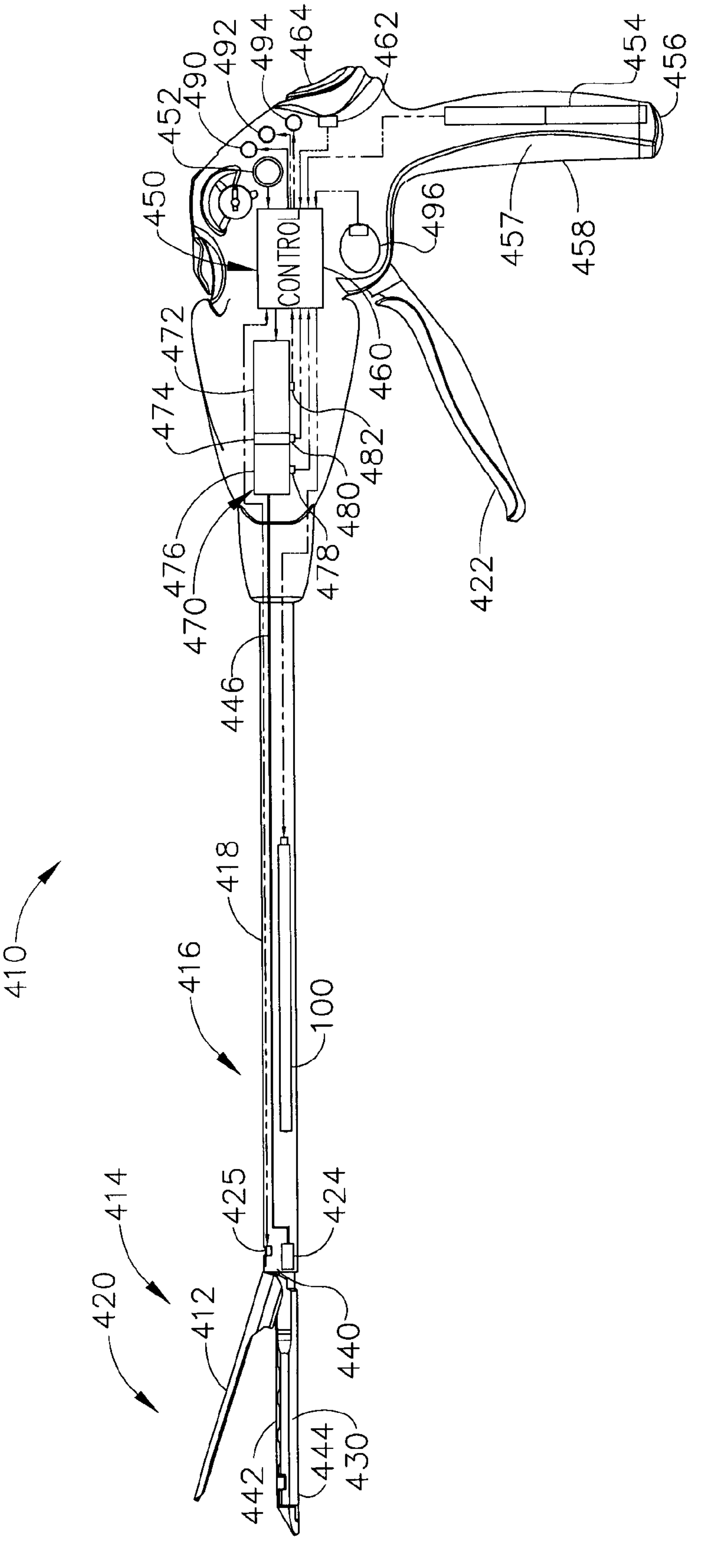
FIG. 19 is a left side view of an alternative surgical stapling and severing instrument of FIG. 1 partially cut away and depicting control circuitry and controls.

In FIG. 19, an alternate surgical stapling and severing instrument 410 that is capable of practicing the unique benefits of the present invention, including both fluid actuation (e.g., opening, closing/clamping) of an upper jaw (anvil) 412 of an end effector 414 as well as dispensing a medical substance onto tissue as severed. An implement portion 416 is formed by an elongate shaft 418 and the end effector 414, depicted as a stapling assembly 420. The surgical stapling and severing instrument 410 also includes a handle 422 attached proximally to the shaft 418. The handle 422 remains external to the patient as the implement portion 416 is inserted through a surgical opening, or especially a cannula of a trocar that forms a pneumoperitoneum for performing a minimally invasive surgical procedure.

A fluid actuator bladders (lift bag) 424 is supported within a staple channel 430 beneath a proximally directed lever 440 that projects such that filling the fluid actuator bladder 424, 26 causes the anvil 412 to pivot like a teeter-totter toward a staple cartridge 442 held in an distal portion 444 of the staple channel 430. Evacuation and collapse of the fluid actuator bladder 424 is assisted by a resilient pressure transducer 425 positioned above the anvil lever 440 in opposition to the fluid actuator bladder 424, urging fluid to flow proximally through a fluid conduit 446.

Control circuitry 450 is powered when enabled by an ON/OFF switch 452 to electrically connect batteries 454 that are physically accessed via a battery cap 456 that closes a battery compartment 457 in a pistol grip 458 of the handle 422. A controller (e.g., microcontroller, programmed logic array, analog control circuit, etc.) 460 receives electrical signals from switches that are actuated by a user or from sensors that indicate a state of the instrument 410. For instance, a thumb button pressure sensor 462 contacting a thumb button 464 senses a closure command. This closure command signal may be a discrete open/close signal or a more continuous value indicating intermediate degrees of closure. Alternatively, the controller 460 may sense a first depression of the thumb button 464 to close and sense a second depression of the thumb button 464 to then open.

The controller 460 responds to the closure signal by activating an electrical fluid control, which in the illustrative version is an EAP syringe actuator 470 containing an EAP stack actuator 472 that translates a plunger 474 within a cylinder 476 to dispense fluid through the fluid conduit 446. The cylinder 476 may be advantageously sized to produce a desired fluid flow rate at a desired fluid pressure to effect closure without excessive pressure if too much tissue is grasped.

The pressure of the fluid may be advantageously sensed by a fluid pressure transducer 478 attached to the cylinder 476 and/or by sensing movement of the anvil 412 from the resilient pressure transducer 425. Alternatively or in addition, fluid volume transferred may be advantageously sensed, such as by Hall effect transducers 480, 482 attached to the cylinder 476 to sense a target incorporated into the plunger 474. The controller 460 may provide indications to the surgeon via an alphanumeric display (not shown) or via a plurality of LEDs, such as a POWER LED 490, an ANVIL POSITION LED 492, and FAULT LED 494. The controller 460 may also sense firing, such as a trigger sensor 496, and in response thereto command the EAP medical substance dispenser 100 to dispense.

Figure 20:
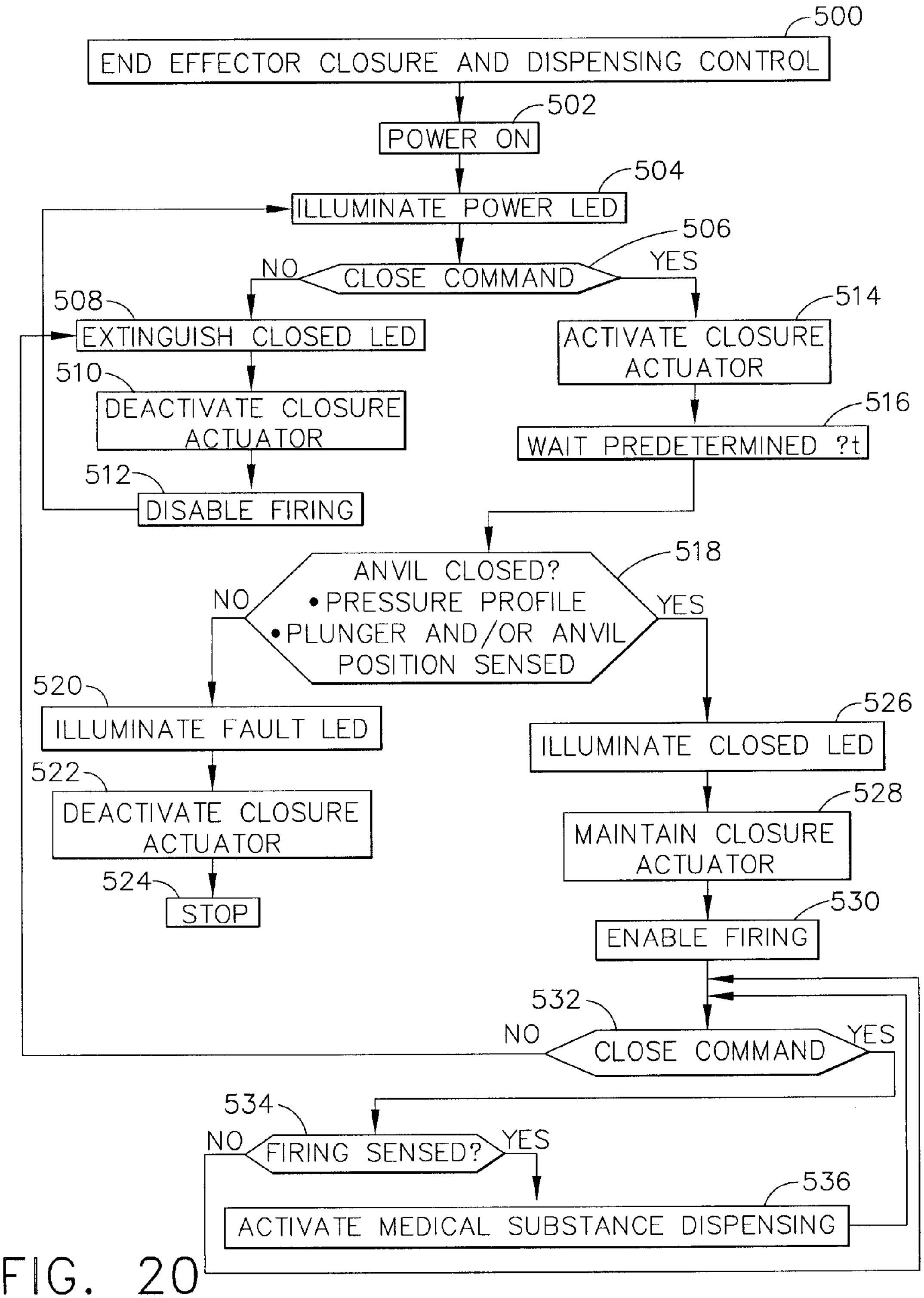
FIG. 20 is a flow diagram of a sequence of operations performed by control circuitry of the surgical stapling and severing instrument of FIG. 19.

In use, as depicted in FIG. 20, an end effector closure and dispensing control procedure, or sequence of operations, 500 is performed by the control circuitry 460 of FIG. 19. In response to power being supplied (block 502), the POWER LED is illuminated (FIG. 504). A determination is made as to whether a close command has been sensed (block 506). If not, a CLOSED LED is extinguished (if lit) (block 508). The closure actuator is deactivated (if currently activated) to allow resilient opening of the anvil (block 510). Firing is disabled (FIG. 512) and processing loops back to block 504 to continue waiting for a close command. If a close command is sensed in block 506, then the closure actuator is activated (block 514) and a predetermined time elapses waiting for the anvil to respond (block 516). Then a determination is made in block 518 as to whether successful closing has occurred, such as by comparing a pressure profile or by sensing a position (e.g., anvil, anvil). If not satisfied, then the FAULT LED is illuminated (block 520). The closure actuator is deactivated (block 522) and processing stops (block 524). User intervention may require cycling of power to reset the device. If in block 518 the anvil was successfully closed, then the CLOSED LED is illuminated (block 526). The closure actuator is maintained in this closed condition (block 528), which may be assisted by a clamping lock that allows deactivating the closure actuator. Firing is enabled (block 530). Then a determination is made as to whether the close command is still present (block 532). If not, processing loops back to block 504 to open the end effector. If still closed in block 532, then a further determination is made as to whether firing of the end effector is sensed (block 534). If so, medical substance dispensing is activated (block 536). Else, processing loops back to block 532 to continue waiting for firing.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a non-articulating shaft is described herein for clarity, it should be appreciated that fluid actuated end effector and/or medical substance dispensing may be incorporated into an articulating shaft. In particular, flexible fluid conduits may be incorporated that pass through an articulation joint of a shaft. Alternatively, passages may be formed in a flex-neck type articulation joint to transfer fluid there through.

As another example, while both medical substance dispensing and fluid actuated anvil closing are illustrated herein, applications consistent with aspects of the invention may include either of these features. Further, for applications in which an adhesive and/or cauterizing medical substance is dispensed, it should be appreciated that features such as staples may be omitted.

As another example, while a staple applying assembly 20 is illustrated herein, it should be appreciated that other end effectors (graspers, cutting devices, etc.) may benefit from either or both of fluid controlled closing and medical substance dispensing.

As yet another example, a receptacle for the EAP syringe may be formed in the handle rather than in the elongate shaft.

While an electroactive polymer plunger has various advantages, it should be appreciated that other types of electrically actuated devices may be employed to dispense a medical substance through the elongate shaft to the end effector.

As yet an additional example, a symmetric arrangement for a second EAP syringe may be formed in the elongate channel so that two medical substances may be simultaneously dispensed during firing.

As yet a further example, while a staple applying apparatus provides an illustrative embodiment, it should be appreciated that other endoscopic instruments may benefit from the ability to dispense a liquid at or near a distal end thereof. Examples of instruments that may benefit include, but are not limited to, an ablation device, a grasper, a cauterizing tool, an anastomotic ring introduction device, a surgical stapler, a linear stapler, etc. As such, those instruments that do not employ a firing bar that serves herein as a convenient fluid passage to a cutting surface may instead incorporate ducting or fluid conduits to an appropriate location.

While an electroactive polymer plunger has various advantages, it should be appreciated that other types of electrically actuated devices may be employed to dispense a medical substance through the elongate shaft to the end effector.

As yet an additional example, a fluid actuator bladder that is constrained within a recess of the elongate shaft may be substituted with a cylinder and piston ram.

Figure 21:
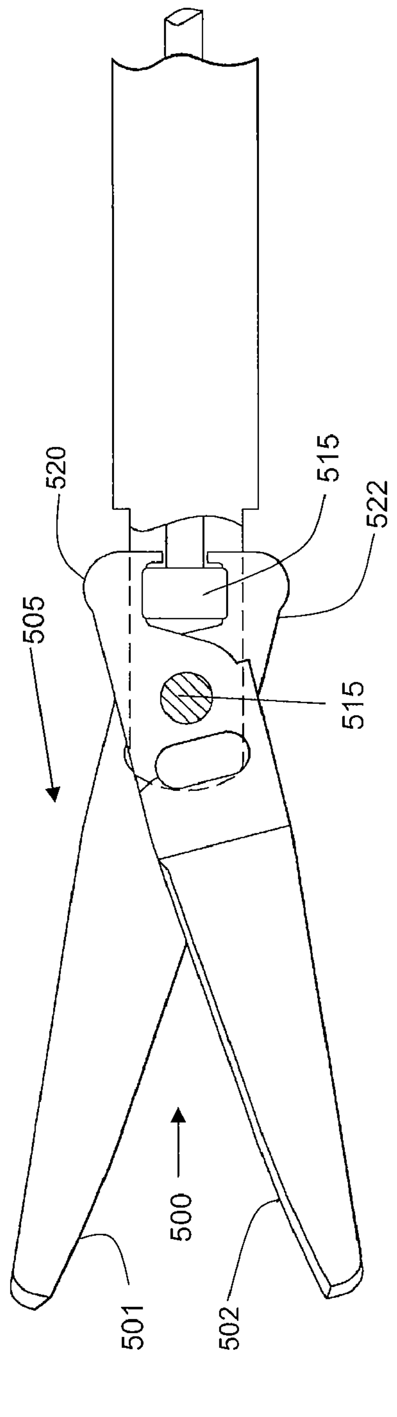
FIG. 21 is an enlarged left side detail view of an end effector with a pair of pivoting members in a scissors like arrangement.

It should be appreciated that in some applications consistent with the invention, both pivoting members 501, 502 of an end effector 500 pivot with respect to a distal end 505 of the end effector 510 in a scissor-like arrangement as shown in FIG. 21. Thus, a fluid actuator bladder 515 may be positioned to assert a force to separate or to draw together respective levers 520, 522 proximally projecting from a pivoting connection 530 of these pivoting members 500, 502 to effect closure (e.g., grasping, cutting) or opening.

As an alternative, it should be appreciated that a fluid actuator bladder may be positioned distal to the pivotal engagement between opposing jaws to urge the jaws open.

As another example, although a handle 22 for direct manipulation by a surgeon is depicted for clarity, a robotically positioned instrument consistent with aspects of the invention may advantageously take advantage of the electrical control and sensing with fluid transfer actuation as described herein.

What is claimed is:

1. A surgical instrument, comprising:

a handle operably configured to produce closure actuation and opening actuation;

an elongate shaft attached to the handle and defining a longitudinal axis;

an end effector distally attached to the elongate shaft and comprising a pair of pivoting members opposingly contacting tissue, wherein the lower pivoting member comprises a staple channel and the upper pivoting member comprises an anvil, and each pivoting member including a respective proximally projecting lever constrained to pivot relative to the other lever about a pivot connection, wherein the lever projecting proximally from the staple channel comprises a frame of the elongate shaft attached to the handle and the lever projecting proximally from the anvil comprises an anvil lever;

a staple cartridge received in the staple channel;

a firing bar slidingly received in the elongate channel and distally movable through the closed end effector to effect severing and stapling of clamped tissue;

an outer sheath encompassing the frame of the elongate shaft and the lever of the anvil; and a fluid actuated closure mechanism comprising:

a fluid actuator bladder positioned between the levers proximal to the pivot connection to operably engage with one or more of the respective proximal projecting levers of the pair of pivoting members, a fluid conduit communicating fluid with the fluid actuator bladder and extending through the elongate shaft, a fluid reservoir responsive to the closure actuation by the handle to selectively and bi-directionally transfer fluid across the fluid conduit to move at least a portion of the fluid actuator bladder laterally to the longitudinal axis to close and open the end effector, and an opposing fluid actuator bladder positioned between the anvil lever and the outer sheath for opposing the fluid actuator positioned between the proximal projecting levers to close the anvil, the handle further operatively configured to differentially expand and compress the opposing fluid actuator bladder and the fluid actuator bladder to move the anvil open and closed.

2. The surgical instrument of claim 1, wherein the handle is operably configured to produce a reciprocating mechanical closure motion, the fluid reservoir selectively compressed and expanded by the reciprocating mechanical closure motion.

3. The surgical instrument of claim 1, wherein the fluid reservoir further comprises an electroactive polymer actuated bi-directional fluid pump operatively actuated by the closure actuation.

4. The surgical instrument of claim 1, wherein the pair of pivoting members comprise cutting blades opposingly cutting tissue.

5. The surgical instrument of claim 1, wherein the pair of pivoting members comprise grasping jaws.

6. The surgical instrument of claim 1, wherein the shaft further comprises an articulation joint, wherein the fluid conduit further comprises a flexible portion traversing the articulation joint.

7. The surgical instrument of claim 1, wherein the handle is operably configured to produce a reciprocating mechanical closure motion, the fluid reservoir selectively compressed and expanded by the reciprocating mechanical closure motion.

8. The surgical instrument of claim 1, further comprising control circuitry response to the closure action by the handle to selectively produce a closure signal, the fluid reservoir further comprising an electroactive polymer actuated bi-directional fluid actuator.

9. The surgical instrument of claim 1, further comprising a monitoring system operatively configured to sense an end effector blocked condition wherein the pair of pivoting members are in a relative position that does not correspond to a commanded position.

10. The surgical instrument of claim 9, wherein the monitoring system further comprises control circuitry responsive to a comparison of a sensed commanded position and a sensed current end effector position.

11. The surgical instrument of claim 10, wherein the monitoring system further comprises position sensing of at least one of the pivoting members.

12. The surgical instrument of claim 10, wherein the monitoring system further comprises pressure sensing positioned to respond to a fluid pressure in the fluid actuated closure mechanism.

13. A surgical instrument, comprising:

a handle operably configured to produce a bi-directional fluid motion from a handle chamber, and to produce a longitudinal firing motion;

an elongate shaft attached to the handle and comprising a fluid conduit communicating with the handle chamber to conduct the bi-directional fluid motion as a fluid pressure, the elongate shaft defining a longitudinal axis and;

an end effector distally attached to the elongate shaft and comprised of a staple channel and an anvil for clamping tissue, wherein each of the staple channel and anvil is operably connected to the other about a pivot to open and close the end effector and each of the staple channel and anvil further comprises a proximal portion extending proximal to the pivot, wherein the proximal portion extending from the staple channel comprises a frame of the elongate shaft attached to the handle, and the proximal portion extending from the anvil includes a lever proximally projecting from the pivot;

a firing bar slidingly received for reciprocating motion in the elongate shaft to transfer the longitudinal firing motion from the handle, and distally terminating in a cutting surface to sever the clamped tissue in the end effector;

a staple cartridge received in the staple channel and responsive to movement of the firing bar to drive and form staples through the clamped tissue;

an outer sheath encompassing the frame of the elongate shaft and the lever of the anvil; and a fluid actuated closure mechanism comprising:

a fluid actuator bladder positioned between the lever and the staple channel to close the anvil, the fluid actuator bladder in fluid communication with the fluid conduit and proximate to the pivot and operatively coupled to at least one of the proximal portions of the end effector to selectively open and to close the end effector in response to the bi-directional fluid motion from the handle chamber via the fluid pressure from the fluid conduit which extends through the elongate shaft, wherein when the fluid pressure from the handle chamber laterally expands at least a portion of the fluid actuator bladder relative to the longitudinal axis, the end effector closes, and when the fluid pressure laterally collapses at least a portion of the fluid actuator bladder relative to the longitudinal axis, the end effector opens, and an opposing fluid actuator bladder positioned between the lever extending proximally from the anvil and the outer sheath for opposing the fluid actuator bladder positioned between the lever and the staple channel to close the anvil, the handle further operatively configured to differentially expand and compress the opposing fluid actuator bladder, and the fluid actuator bladder configured to move the anvil open and closed.

14. The surgical instrument of claim 13, wherein the handle is operably configured to produce a reciprocating mechanical closure motion, the handle chamber selectively compressed and expanded by the reciprocating mechanical closure motion.

15. The surgical instrument of claim 13, further comprising control circuitry response to the closure action by the handle to selectively produce a closure signal, the handle chamber further comprising an electroactive polymer actuated bi-directional fluid pump.

16. A surgical instrument, comprising:

a handle operably configured to produce fluid motion in response to opening and closure actuation;

an elongate shaft attached to the handle and having a longitudinal axis;

first and second tissue contacting members pivotally engaged to each other about a pivot and distally projecting from the elongate shaft, wherein the first tissue contacting member comprises a staple channel and the second tissue contacting member comprises an anvil, each of said tissue contacting members having a proximal portion extending proximally from the pivot, wherein the proximal portion of the staple channel comprises a frame of the elongate shaft attached to the handle, and the proximal portion of the anvil comprises a lever extending proximally from the pivotal engagement;

a staple cartridge received in the staple channel;

a firing bar slidingly received in the elongate channel and distally movable through the closed end effector to effect severing and stapling of clamped tissue;

an outer sheath encompassing the frame of the elongate shaft and the lever of the anvil; and a fluid actuated closure mechanism comprising:

a fluid actuator bladder located between and coupled between the first and second tissue contacting members, the fluid actuator bladder positioned proximal to the pivot and operably engaging one or more of the proximal portion of the first and second tissue contacting members, a fluid conduit communicating with the fluid actuator bladder, the fluid conduit extending through the elongate shaft, a fluid reservoir in fluid communication with the fluid conduit and responsive to the closure actuation of the handle, the closure motion selectively and bi-directionally transferring fluid across the fluid conduit to close and open the end effector by expanding and contracting at least a portion of the fluid actuator bladder in a direction lateral to the longitudinal axis, and an opposing fluid actuator bladder positioned between the anvil lever and the outer sheath for opposing the fluid actuator bladder positioned between the proximal portions of the first and second tissue contacting members to close the anvil, the handle further operatively configured to differentially expand and compress the opposing fluid actuator bladder and the fluid actuator bladder to move the anvil open and closed.

17. The surgical instrument of claim 16, wherein the elongate shaft includes a lever cavity receiving the lever, the fluid actuator bladder positioned in the lever cavity.

* * * * *